United States Patent [19]

Jobe

[11] Patent Number: 4,738,355
[45] Date of Patent: Apr. 19, 1988

[54] CONTAINER FOR INTRAOCULAR LENSES AND CONTACT LENSES

[75] Inventor: Michael J. Jobe, Forth Worth, Tex.

[73] Assignee: Alcon Laboratories, Inc., Fort Worth, Tex.

[21] Appl. No.: 946,000

[22] Filed: Dec. 24, 1986

[51] Int. Cl.⁴ .......................... B65D 81/22; A61F 1/16
[52] U.S. Cl. ....................................... 206/5.1; 206/438; 215/6; 623/6
[58] Field of Search ..................... 623/6; 206/5.1, 438; 215/6

[56] References Cited

U.S. PATENT DOCUMENTS

| | | | |
|---|---|---|---|
| 537,146 | 4/1895 | Froehlich | 206/438 X |
| 2,301,710 | 11/1942 | Scudder | 206/438 X |
| 4,254,509 | 3/1981 | Tennant | . |
| 4,332,318 | 6/1982 | Feldman | 206/5.1 |
| 4,573,998 | 3/1986 | Mazzocco | 623/6 |

FOREIGN PATENT DOCUMENTS

| | | | |
|---|---|---|---|
| 503143 | 5/1951 | Belgium | 215/6 |
| 0136807 | 4/1985 | European Pat. Off. | . |
| 84903 | 3/1965 | France | 215/6 |
| 13654 | 2/1974 | Japan | 206/5.1 |
| 4616 | 3/1900 | United Kingdom | 215/6 |

Primary Examiner—William Price
Attorney, Agent, or Firm—James A. Arno; Gregg C. Brown

[57] ABSTRACT

A two compartment container adapted for the packaging of intraocular lenses, contact lenses and other small, delicate devices requiring hydrated storage is described. The devices are contained in a first, upper compartment, while a second, lower compartment contains a fluid. The two compartments are placed in fluid communication with each other by means of a narrow passage which prevents the devices in the first compartment from entering the second compartment.

12 Claims, 1 Drawing Sheet

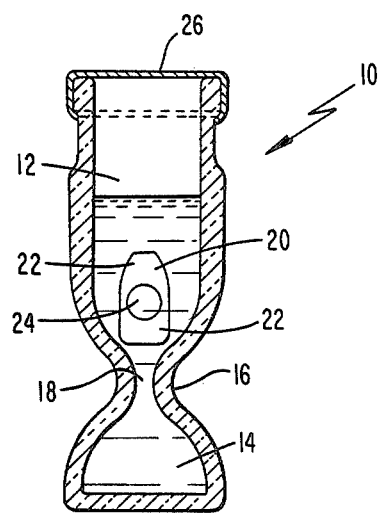

CONTAINER FOR INTRAOCULAR LENSES AND CONTACT LENSES

BACKGROUND OF THE INVENTION

The present invention relates to containers for initial holding and eventual dispensing of intraocular lenses and contact lenses, particularly such lenses made from hydrogels or other similar, soft materials. Such intraocular lenses are described in U.S. Pat. Nos. 4,254,509 (Tennant) and 4,573,998 (Mazzocco) and in European patent application No. 136,807 (Barrett). Reference is made to these publications for further background concerning intraocular lenses made from hydrogels. Because hydrogels have a relatively high water content, it is normally necessary to store these lenses in a physiologically acceptable, sterile fluid prior to use, so that the lenses do not become dehydrated and brittle. Such storage is also a requirement in connection with the packaging of contact lenses made from hydrogels.

Intraocular lenses are very small, with maximum dimensions (e.g., widths) generally on the order of 15 millimeters or less, and frequently 12 millimeters or less. The small size of these lenses can complicate their removal from a container. More particularly, it can be very difficult to locate the lens in a fluid-filled container and/or grasp the lens and remove it from the container. This difficulty represents a significant problem, since ease of removal of a lens from its container is critical to the convenience of the ophthalmic surgeon and is necessary to facilitate prompt delivery of the lens to the surgeon so that surgical implantation of the lens in the eye of the patient is not delayed or otherwise complicated by difficulties encountered in removing the lens from its container. Similar difficulties are encountered when removing contact lenses from fluid-filled containers.

SUMMARY OF THE INVENTION

A principal objective of the present invention is the provision of containers for intraocular lenses which are designed to contain the lenses and a fluid bathing the lenses in a manner such that the lenses may be readily located, grasped and removed from the containers. A further objective of the present invention is the provision of such containers for contact lenses.

The foregoing objectives and other general objectives of the present invention are achieved by the provision of a container which comprises a first compartment containing one or more lenses and a sterile, physiologically acceptable fluid, a second compartment beneath the first compartment which contains only fluid, and a channel between said first and second compartments which allows fluid to flow between these compartments but prevents the lens or lenses contained in the first compartment from entering the second compartment. In a preferred embodiment of the present invention, the container has a configuration which generally resembles an hour-glass, with an opening located at the top of the container and the second compartment located at the bottom of the container.

The containers of the present invention have several advantages over single compartment containers having a flat bottom. First, the generally conical shape of the first compartment makes it easier to locate and grasp the lens or lenses contained therein, as compared to prior art containers having a flat bottom surface which allow the lens to assume a horizontal position on the bottom of the container. The configuration of the first compartment of the present containers causes the lenses to assume a generally vertical orientation in the container; this orientation facilitates grasping of the lens to easily remove the lens from the container. A second major advantage of the present containers is that the containers can be manipulated in a manner such that fluid from the second compartment will flush the lens from its position in the bottom of the first compartment. This flushing may be of assistance in locating and removing the lens.

BRIEF DESCRIPTION OF DRAWING

The sole FIGURE of drawing is a cross-sectional view of a container according to the present invention.

DESCRIPTION OF PREFERRED EMBODIMENT

Referring now to the drawing, it will be seen that a container according to the present invention 10 comprises an upper or first compartment 12 and a lower or second compartment 14. These compartments are separated by a narrowed portion 16. The narrowed portion 16 includes a channel 18 between the first compartment 12 and the second compartment 14 which places these compartments in fluid communication with each other. The channel 18 must be narrow enough so that an intraocular lens 20 contained in the first compartment 12 cannot travel through the channel into the second compartment 14. This requirement means that the width of the channel 18 must be less than the smallest dimension (i.e., length or width) of the lens contained in the first compartment.

The container 10 is sealed by a cap 26 covering the opening or mouth of the container. In the embodiment illustrated, the cap 26 is made from aluminum and is in sealing engagement with a lip around the mouth of the container. Other means for closure, such as a threaded cap which engages with complementary threads around the exterior of the container mouth, are equally acceptable. Still further means for closing the container in a sealed manner will be readily apparent to those skilled in the art.

The intraocular lens 20 may be placed in the container 10 as follows. A physiologically acceptable fluid is placed in the container 10 in an amount sufficient to fill the second compartment completely and fill the first compartment to at least a point at which the lens 20 will be entirely covered when placed therein. The lens is then placed in the first compartment, additional fluid is added if needed, and the container 10 is sealed by attaching the cap 26 to the mouth of the container. The container and its contents are then sterilized by means of autoclaving.

The intraocular lens 20 may be removed from the container 10 as follows. Prior to removing the cap 26, the lens 20 is visually located in the first compartment 12. Once the lens 20 is located, it may be necessary to agitate the container if the lens is not moving freely in the fluid in the first compartment 12. When it is determined that the lens 20 is moving freely in the first compartment 12, the cap 26 is removed. The lens 20 is then removed by grasping a flange portion 22 of the lens with a sterilized tweezer or other suitable instrument, taking care not to damage the optical portion 24 of the lens.

The containers of the present invention may be manufactured by crimping a piece of tubular material to form a first compartment and a second compartment separated by a narrow channel at the point of the crimping. The tubular material may be any transparent material conventionally used for packaging, but will preferably be glass. If glass is utilized, the container is formed by heating a section of glass tubing to a softened state and crimping the tubing at or near its midsection while it is soft to form two compartments. One end of the tubing is then closed, and the other end is provided with threads or other means (e.g., a lip) to engage and secure a cap which will close and seal the container.

The present invention has been described above in connection with a preferred embodiment. Obvious variations of that embodiment will be readily apparent to those skilled in the art. For example, the containers of the present invention have been primarily described in connection with packaging of intraocular lenses and contact lenses, but may be equally useful in packing other devices, such as any other medical or nonmedical device which is relatively small, delicate, and required to be packaged in a fluid.

What is claimed is:

1. A container suitable for use in the packaging of intraocular lenses and contact lenses, comprising a first compartment having a substantially conical configuration with its apex oriented downwardly toward the bottom of the container, said first compartment being sized and adapted to receive and contain the solid contents to be placed in said container and a portion of the fluid contents to be placed in said container; a second compartment located beneath said first compartment and in fluid communication with said first compartment, said second compartment being sized and adapted to be completely filled by a portion of the fluid contents to be placed in said container; passage means between the first and second compartments to place said compartments in fluid communication with each other, said passage means being sized and adapted to prevent the solid contents to be placed in said first compartment from entering said second compartment; and closure means sized and adapted to seal an opening in said container located at the upper end of said first compartment.

2. A container according to claim 1, wherein an intraocular lens is contained in the first compartment and a physiologically acceptable fluid is contained in the first and second compartments.

3. A container according to claim 2, wherein the intraocular lens is made from a hydrogel.

4. A container according to claim 1, wherein a contact lens is contained in the first compartment and a physiologically acceptable fluid is contained in the first and second compartments.

5. A method of packing an intraocular lens which comprises placing the lens in a container according to claim 1.

6. A method of packaging a contact lens which comprises placing the lens in a container according to claim 1.

7. A container suitable for use in the packaging of intraocular lenses and contact lenses, comprising a generally cylindrical, hollow body having a closed end and an open end; a first compartment disposed at the open end of said container, said first compartment having a substantially conical configuration with its apex directed toward the closed end of said container; a second compartment disposed at the closed end of said container; passage means disposed between the first and second compartments to place said compartments in fluid communication with each other, said passage means being sized and adapted to prevent the solid contents to be placed in said first compartment from entering said second compartment; and closure means sized and adapted to seal the open end of said container.

8. A container according to claim 7, wherein an intraocular lens is contained in the first compartment and a physiologically acceptable fluid is contained in the first and second compartments.

9. A container according to claim 8, wherein the intraocular lens is made from a hydrogel.

10. A container according to claim 7, wherein a contact lens is contained in the first compartment and a physiologically acceptable fluid is contained in the first and second compartments.

11. A method of packaging an intraocular lens which comprises placing the lens in a container according to claim 7.

12. A method of packaging a contact lens which comprises placing the lens in a container according to claim 7.

* * * * *